United States Patent
Vranes et al.

(10) Patent No.: US 11,149,304 B2
(45) Date of Patent: Oct. 19, 2021

(54) METHOD FOR DETERMINING NUCLEIC ACID DEGRADATION IN A SAMPLE IN WHICH AT LEAST TWO OVERLAPPING AMPLICONS ARE PRODUCED AND TWO PROBES ARE USED IN THE METHOD

(71) Applicant: QIAGEN GmbH, Hilden (DE)

(72) Inventors: Miroslav Vranes, Hilden (DE); Ralf Peist, Hilden (DE); Mario Scherer, Hilden (DE); Stefan Otto Cornelius, Hilden (DE)

(73) Assignee: Qiagen GmbH, Hilden (DE)

(*) Notice: Subject to any disclaimer, the term of this patent is extended or adjusted under 35 U.S.C. 154(b) by 175 days.

(21) Appl. No.: 16/333,043

(22) PCT Filed: Sep. 15, 2017

(86) PCT No.: PCT/EP2017/073323
§ 371 (c)(1),
(2) Date: Mar. 13, 2019

(87) PCT Pub. No.: WO2018/050844
PCT Pub. Date: Mar. 22, 2018

(65) Prior Publication Data
US 2019/0264256 A1   Aug. 29, 2019

(30) Foreign Application Priority Data
Sep. 16, 2016   (EP) .................................... 16189217

(51) Int. Cl.
*C12Q 1/68* (2018.01)
*C12Q 1/6851* (2018.01)
*C12Q 1/6806* (2018.01)

(52) U.S. Cl.
CPC ......... *C12Q 1/6851* (2013.01); *C12Q 1/6806* (2013.01); *C12Q 2531/113* (2013.01); *C12Q 2537/143* (2013.01); *C12Q 2545/114* (2013.01)

(58) Field of Classification Search
CPC ....................................................... C12Q 1/68
(Continued)

(56) References Cited

U.S. PATENT DOCUMENTS

2005/0272080 A1*  12/2005 Palma .................. C12Q 1/6883
                                                            435/6.11
2006/0281108 A1    12/2006 Monforte et al.
(Continued)

FOREIGN PATENT DOCUMENTS

EP    1572962 A2 *  9/2005  ........... C12N 15/113
FR    2929292 A1 * 10/2009  ........... C12Q 1/6883
(Continued)

OTHER PUBLICATIONS

International Search Report dated Dec. 4, 2017 filed in PCT/EP2017/073323.
(Continued)

*Primary Examiner* — Aaron A Priest
(74) *Attorney, Agent, or Firm* — Rankin, Hill & Clark LLP

(57) ABSTRACT

The present invention relates to a method for assessing the status of nucleic acid degradation and/or integrity of one or more nucleic acids in a sample, comprising the steps amplifying at least two overlapping regions within at least one locus (e.g. by heminested or nested PCR), and detecting the amount of the at least two amplification products through the use of at least two probes, wherein one probe binds to the region of overlap and the at least one other probe binds to a non-overlapping region. The invention further relates to a method of designing primers and/or probes for amplifying at
(Continued)

Two genomic regions targeted on one genomic locus genomic regions targeted on one genomic locus P = probe for detection least two overlapping regions within at least one locus, wherein the locus that is amplified is a single copy locus (SCL) or multicopy locus (MLC). The invention also relates to a primer and a primer pair for amplifying at least two overlapping regions from one nucleic acid template which is a multicopy locus present in 21 loci in the human genome. These primers and probes may be in a kit. Hence, the invention also relates to a kit for assessing the status of nucleic acid degradation and/or integrity of one or more nucleic acids in a sample.

21 Claims, 10 Drawing Sheets

Specification includes a Sequence Listing.

(58) Field of Classification Search
USPC ........................................... 435/6.12
See application file for complete search history.

(56) References Cited

U.S. PATENT DOCUMENTS

| 2010/0129896 | A1* | 5/2010 | Knapp | C12Q 1/686 |
| | | | | 435/285.1 |
| 2013/0078639 | A1 | 3/2013 | Morris | |
| 2013/0224742 | A1 | 8/2013 | Wende et al. | |
| 2014/0147843 | A1 | 5/2014 | Di Pasquale et al. | |

FOREIGN PATENT DOCUMENTS

| WO | WO-9854318 | A1 * | 12/1998 | ......... C07K 14/4703 |
| WO | 2006119439 | A2 | 11/2006 | |
| WO | WO-2006119439 | A2 * | 11/2006 | ........... C12Q 1/6848 |
| WO | WQ-2009144424 | A2 * | 12/2009 | ........... C12Q 1/6883 |
| WO | 2012038503 | A1 | 3/2012 | |
| WO | 2012113577 | A1 | 8/2012 | |
| WO | 2016034231 | A1 | 3/2016 | |

OTHER PUBLICATIONS

"Alzheimers disease diagnostic probe, SEQ ID 13019," Dec. 6, 2012, p. 24; Cited in International Search Report.
"*Homo sapiens* piRNA-51721, complete sequence," Jun. 13, 2006, p. 28; Cited in ISR.
"Sequence 4 from Patent WO9854318," Jan. 21, 2000, p. 25; Cited in ISR.
"Sequence 24058 from Patent EP2904117," Feb. 25, 2016; Cited in ISR.
"Sequence 403567 from Patent EP1572962," Jan. 25, 2015, Cited in ISR.
"Sequence 489211 from patent U.S. Pat. No. 7,374,927," Aug. 26, 2008; Cited in ISR.
J. Nicklas et al. "Development of a Real-Time Method to Detect DNA Degradation in Forensic Samples," Journal of Forensic Sciences, Mar. 2012, pp. 466-471, vol. 57 No. 2, American Academy of Forensic Sciences, US; Cited in ISR.

* cited by examiner

Fig. 1: Two genomic regions targeted on one genomic locus
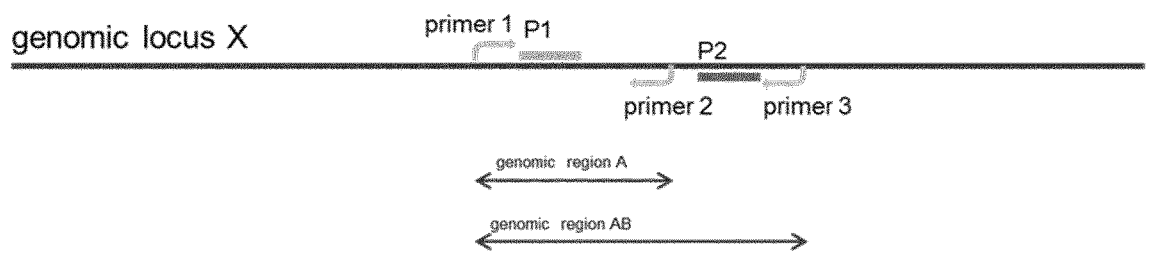
P = probe for detection
Fig. 2: Three genomic regions targeted on one genomic locus
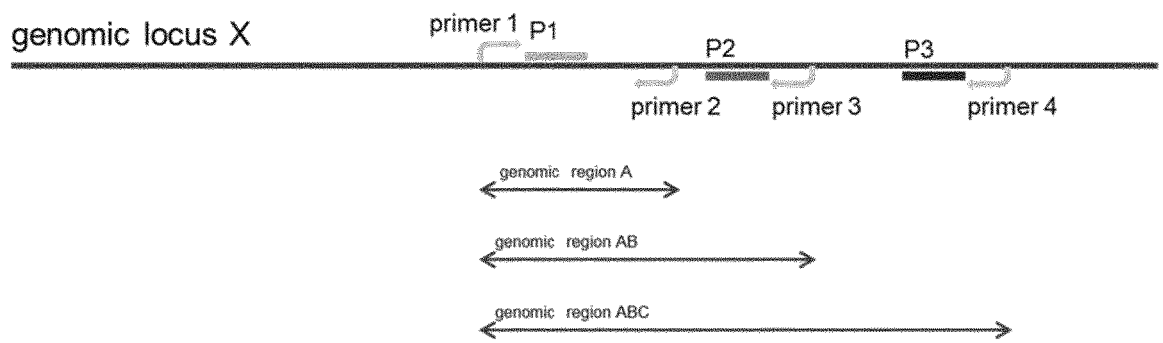
P = probe for detection

Fig. 3: Schematic drawings of state of the art solutions to address DNA degradation or integrity.

A) Two non-overlapping genomic regions targeted on one genomic locus genomic regions targeted on one genomic locus

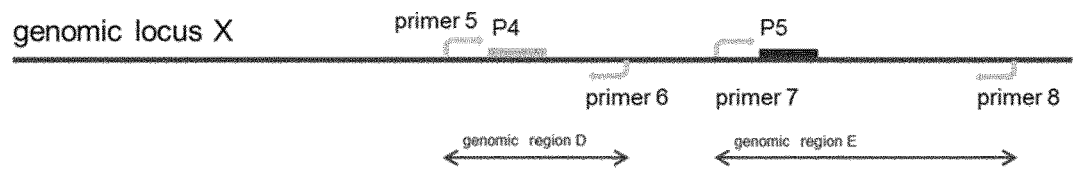

P = probe for detection

B) Two genomic regions targeted on different genomic loci genomic regions targeted on different genomic loci

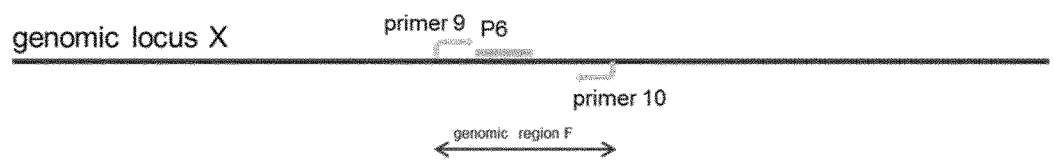

P = probe for detection

Fig. 4: Different measurement methods of degraded DNA in humans
A) Method according to the invention
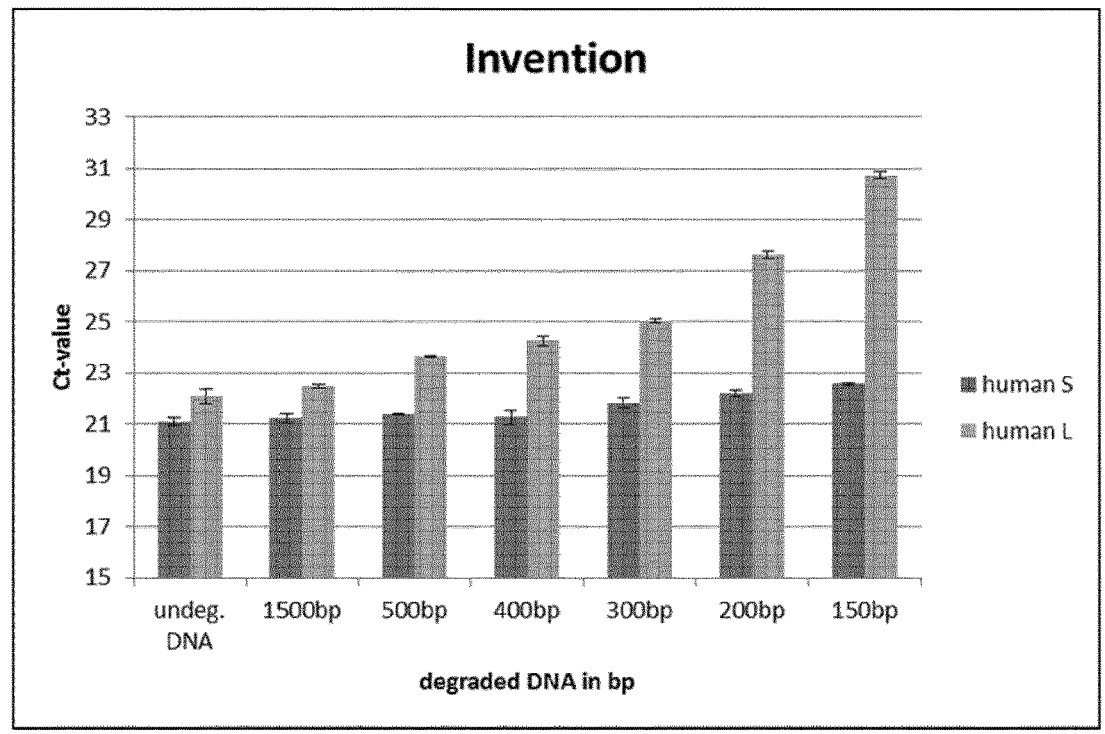
B) Method according to US 9040243B2/EP 10178914
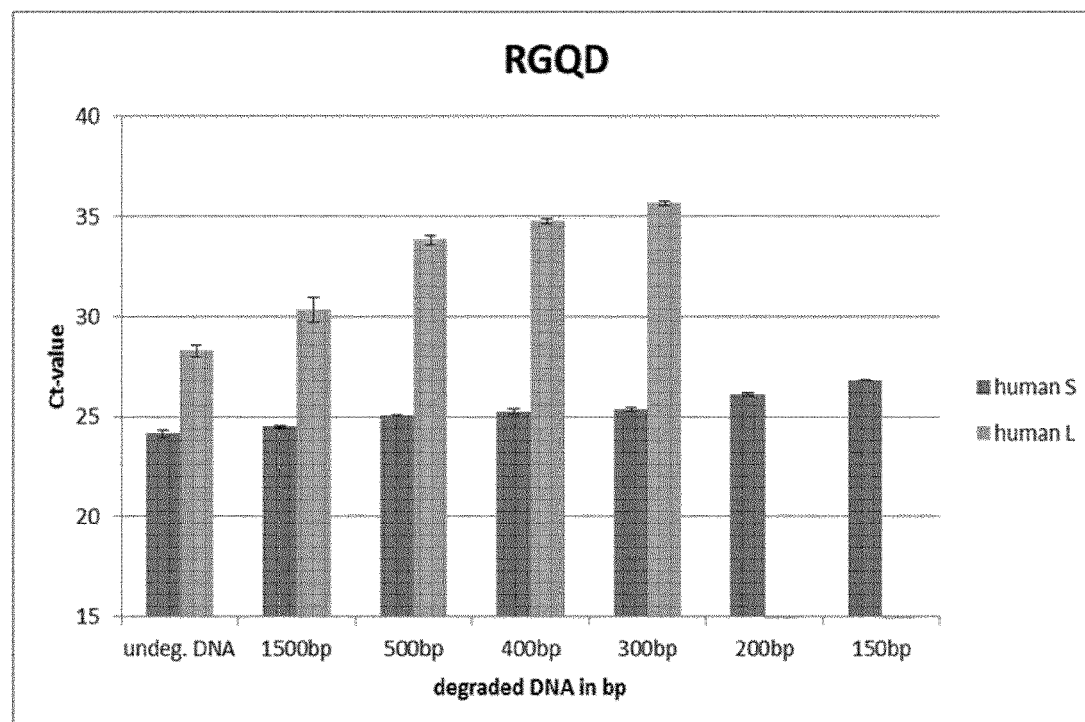

Fig 4: (continued from prior page)
C) Method according to Supplier A
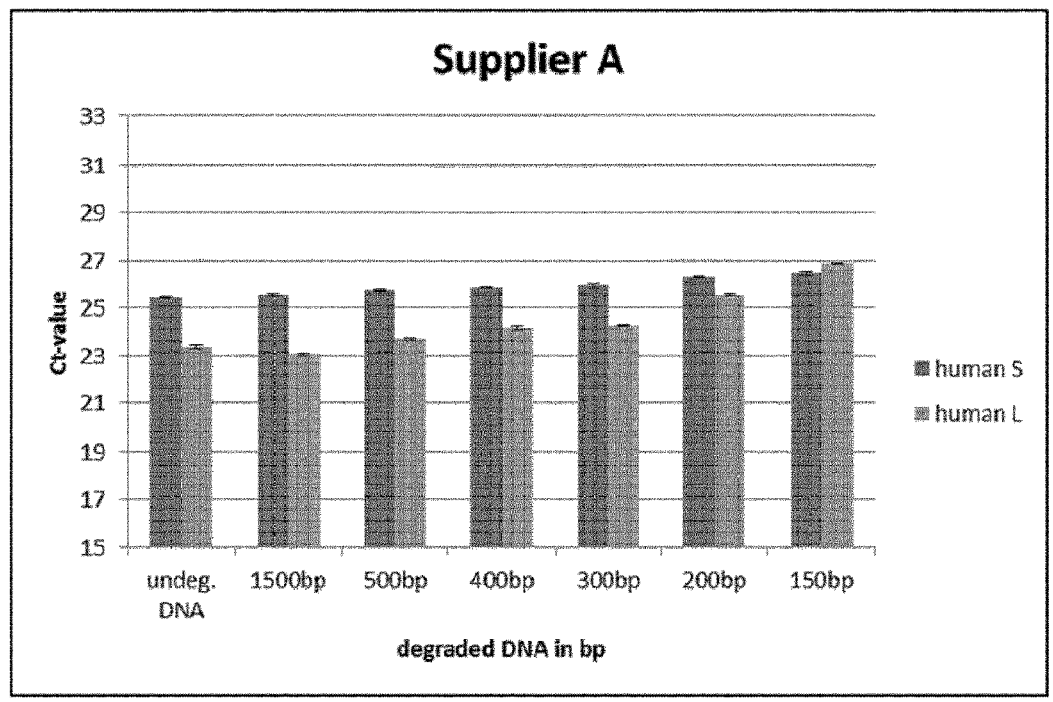
D) Method according to Supplier P
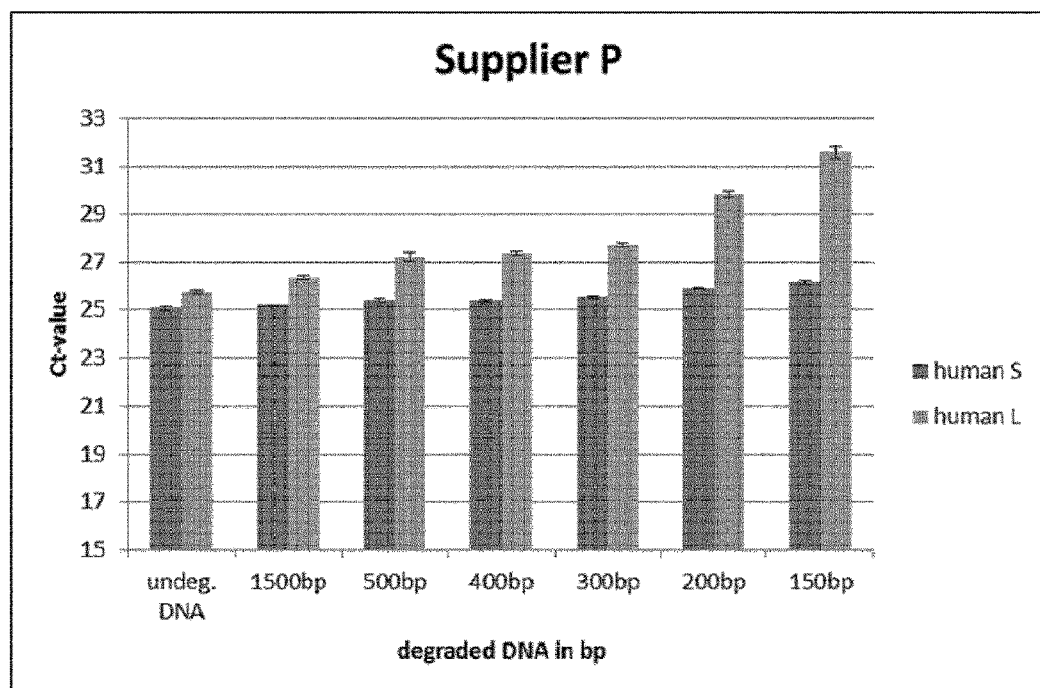

Fig. 5: Comparison of degradation indices between different PCR systems

|  | Invention | RGQD | Supplier A | Supplier P |
|---|---|---|---|---|
| undegraded DNA | 1,0 | 0,7 | 1,0 | 1,0 |
| 1500bp | 1,3 | 1,5 | 0,8 | 1,4 |
| 500bp | 2,8 | 6,5 | 1,0 | 2 |
| 400bp | 3,2 | 9,5 | 1,3 | 2 |
| 300bp | 5,0 | 14,3 | 1,3 | 3 |
| 200bp | 17,5 | NA | 2,4 | 9,4 |
| 150bp | 76,1 | NA | 5,0 | 25,7 |

Fig. 6: Sequences

| SEQ ID NO | Designation | Sequences |
|---|---|---|
| 1 | Primer 1 | CCTGAGGATGCCACAGTGAGACAC |
| 2 | Primer 2 | ACTTCTGTCTACTGTCGGACTCTACAGG |
| 3 | primer 3 | GGCCCAGCTTTGACTTGAGAACAG |
| 4 | probe S | TCTGGAGGGTCCACTGTGAGGCAG |
| 5 | probe L | TCCAGGCCCAGCTCTTGCCTCATG |
| 6 | chr1_KI270763v1_alt:68038+68128 91bp | CCTGAGGATGCCACAGTGAGACACcatctgggtctggagggtccactgtgaggcagaggctggCCTGTAGAGTCCGACAGTAGACAGAAGT |
| 7 | chr17_GL383563v3_alt:4396+4486 91bp | CCTGAGGATGCCACAGTGAGACACcatctgggtctggagggtccactgtgaggcagaggctgaCCTGTAGAGTCCGACAGTAGACAGAAGT |
| 8 | chr11:130033+130123 | CCTGAGGATGCCACAGTGAGACACcatctgggtctggagggtccactgtgaggcagaggctgaCCTGTAGAGTCCGACAGTAGACAGAAGT |
| 9 | chr17:64396+64486 91bp | CCTGAGGATGCCACAGTGAGACACcatctgggtctggagggtccactgtgaggcagaggctgaCCTGTAGAGTCCGACAGTAGACAGAAGT |
| 10 | chr1:243055930+243056020 91bp | CCTGAGGATGCCACAGTGAGACACcatctgggtctggagggtccactgtgaggcagaggctggCCTGTAGAGTCCGACAGTAGACAGAAGT |
| 11 | chr1:222475813+222475903 91bp | CCTGAGGATGCCACAGTGAGACACcatctgggtctggagggtccactgtgaggcagaggctggCCTGTAGAGTCCGACAGTAGACAGAAGT |

(table continues on next page)

Fig. 6: Sequences (continued from prior page)

| | | |
|---|---|---|
| 12 | chr1:728464+728554 91bp | CCTGAGGATGCCACAGTGAGACACcatctgggtctggagggtccactgtgaggcagaggctgaCCTGTAGAGTCCGACAGTAGACAGAAGT |
| 13 | chr1:493558+493648 91bp | CCTGAGGATGCCACAGTGAGACACcatctgggtctggagggtccactgtgaggcagaggctgaCCTGTAGAGTCCGACAGTAGACAGAAGT |
| 14 | chr1:138356+138446 91bp | CCTGAGGATGCCACAGTGAGACACcatctgggtctggagggtccactgtgaggcagaggctgaCCTGTAGAGTCCGACAGTAGACAGAAGT |
| 15 | chr4:119408800+119408890 91bp | CCTGAGGATGCCACAGTGAGACACcatctgggtctgcagggtccactgtgaggcagaggctggCCTGTAGAGTCCGACAGTAGACAcAAGT |
| 16 | chr6:146543+146633 91bp | CCTGAGGATGCCACAGTGAGACACcatctgggtctggagggtccactgtgaggcagaggctggCCTGTAGAGTCCGACAGTAGACAGAAGT |
| 17 | chr7:56377197+56377287 91bp | CCTGAGGATGCCACAGTGAGACACcatctgggtctggagggtccactgtgaggcagaggctggCCTGTAGAGTCCGACAGTAGACAGAAGT |
| 18 | chr7:55746723+55746813 91bp | CCTGAGGATGCCACAGTGAGACACcatctgggtctggagggtccactgtgaggcagaggctggCCTGTAGAGTCCGACAGTAGACAGAAGT |
| 19 | chrUn_KI270745v1:20572-20662 91bp | CCTGAGGATGCCACAGTGAGACACcatctgggtctggagggtccactgtgaggcagaggctgaCCTGTAGAGTCCGACAGTAGACAGAAGT |
| 20 | chr20:64288636-64288726 91bp | CCTGAGGATGCCACAGTGAGACACcatctgggtctggagggtccactgtgaggcagaggctggCCTGTAGAGTCCGACAGTAGACAGAAGT |
| 21 | chr1:227968791-227968881 91bp | CCTGAGGATGCCACAGTGAGACACcatctgggtctggagggtccactgtgaggcagaggctggCCTGTAGAGTCCGACAGTAGACAGAAGT |
| 22 | chr4:118631693-118631783 91bp | CCTGAGGATGCCACAGTGAGACACcatctgggtctggagggtccactgtgaggcagaggctggCCTGTAGAGTCCGACAGTAGACAGAAGT |
| 23 | chr5:181325303-181325393 91bp | CCTGAGGATGCCACAGTGAGACACcatctgggtctggagggtccactgtgaggcagaggctgaCCTGTAGAGTCCGACAGTAGACAGAAGT |
| 24 | chr7:128652424-128652514 91bp | aCTGAGGATGCCACAGTGAGACACcatctgggtctggagggtccactgtgaggcagaggctggCCTGTAGAGTCCGACAGTAGACAGAAGT |

(table continues on next page)

Fig. 6: Sequences (contined from prior page)

| 25 | chr7:637 46664-6374675 4 91bp | CCTGAGGATGCCACAGTGAGACACcatctgggtctggagggtccactgtgaggcagaggctggCCTGTAGAGTCCGACAGTAGACAGAAGT |
|---|---|---|
| 26 | chr7:458 08736-4580882 6 91bp | CCTGAGGATGCCACAGTGAGACACcatctgggtctggagggtccactgtgaggcagaggctggCCTGTAGAGTCCGACAGTAGACAGAAGT |
| 27 | chr1_KI2 70763v1 _alt:680 38+6839 0 353bp | CCTGAGGATGCCACAGTGAGACACcatctgggtctggagggtccactgtgaggcagaggctggcctgtagagtccgacagtagacagaagttgggcaaaaggctgatttgaggaagttttgggcttcaagagtcagccacgaggcaggcactaggcctggaaatggcctgacagtcatgagttgggcctaaatgggccactgtgagggaggagctgtgcctgttgaggctgctggcaggcaggcagaaattcggcctggggcagctgccatgaggcaagagctgggcctggaaaaagcccctgggaggcaagagcagggcctgcagaggCTGTTCTCAAGTCAAGCTGGGCC |
| 28 | chr17_G L383563 v3_alt:4 396+474 8 353bp | CCTGAGGATGCCACAGTGAGACACcatctgggtctggagggtccactgtgaggcagaggctgacctgtagagtccgacagtagacagaagttgggcaaaaggctgatttgaggaagttttgggcttcaagagtcagccacgaggcaggcactaggcctggaaatggcctcacagtcatgagttgggcctaaatgggccactgtgagggaggagctgtgcctgttgaggctgctggcaggcaggcagaaatttggcctggggcagccgccatgaggcaagagctgggcctggaaaaagcccctgggaggcaagagcagggcctgcagaggCTGTTCTCAAGTCAAAGCTGGGCC |
| 29 | chr11:13 0033+13 0385 353bp | CCTGAGGATGCCACAGTGAGACACcatctgggtctggagggtccactgtgaggcagaggctgacctgtagagtccgacagtagacagaagttgggcaaaagcctgatttgaggaagttttgggcttcaagagtcagccacgaggcaggcactaggcctggaaatggcctcacagtcatgagttgggcctaaatgggccactgtgagggaggagctgtgcctgttgaggctgctggcaggcaggcagaaatttggcctggggcagctgccatgaggcaagagctgggcctggaaaaagcccctgggaggcaagagcagggcctgcagaggCTGTTCTCAAGTCAAAGCTGGGCC |
| 30 | chr17:64 396+647 48 353bp | CCTGAGGATGCCACAGTGAGACACcatctgggtctggagggtccactgtgaggcagaggctgacctgtagagtccgacagtagacagaagttgggcaaaaggctgatttgaggaagttttgggcttcaagagtcagccacgaggcaggcactaggcctggaaatggcctcacagtcatgagttgggcctaaatgggccactgtgagggaggagctgtgcctgttgaggctgctggcaggcaggcagaaatttggcctggggcagccgccatgaggcaagagctgggcctggaaaaagcccctgggaggcaagagcagggcctgcagaggCTGTTCTCAAGTCAAAGCTGGGCC |
| 31 | chr1:243 055930+ 2430562 82 353bp | CCTGAGGATGCCACAGTGAGACACcatctgggtctggagggtccactgtgaggcagaggctggcctgtagagtccgacagtagacagaagttgggcaaaaggctgatttgaggaagttttgggcttcaagagtcagccacgaggcaggcactaggcctggaaatggcctgacagtcatgagttgggcctaaatgggccactgtgagggaggagctgtgcctgttgaggctgctggcaggcaggcagaaattcggcctggggcagctgccatgaggcaagagctgggcctggaaaaagcccctgggaggcaagagcagggcctgcagaggCTGTTCTCAAGTCAAAGCTGGGCC |
| 32 | chr1:222 475813+ 2224761 65 353bp | CCTGAGGATGCCACAGTGAGACACcatctgggtctggagggtccactgtgaggcagaggctggcctgtagagtccgacagtagacagaagttgggcaaaaggctgatttgaggaagttttgggcttcaagagtcagccacgaggcaggcactaggcctggaaatggcccgacagtcatgagttgggactaaatgggccactgtgagggaggagctgtgcctgttgaggctgctggcaggcaagcagaaatttggcctcgggcagctgccatgaggcaagagctgggcctggaaaaagcccctgggaggcaagagcagggcctgcagaggCTGTTCTCAAGTCAAAGCTGGGCC |

(table continues on next page)

Fig. 6: Sequences (contined from prior page)

| | | |
|---|---|---|
| 33 | chr1:728464+728816 353bp | CCTGAGGATGCCACAGTGAGACACcatctgggtctggagggtccactgtgaggcagaggctgacctgta gagtccgacagtagacagaagttgggcaaaagcctgatttgaggaagttttgggcttcaagagtcagccacgaggc aggcactaggcctggaaatggactcacagtcatgagttgggcctaaatgggccactgtgagggaggagctgtgcct gttgaggctgctggcaggcaggcagaaatttggcctggggcagctgccatgaggcaagagctgggcctggaaaaa gcccctgggaggcaagagcagggcctgcagaggCTGTTCTCAAGTCAAAGCTGGGCC |
| 34 | chr1:493558+493910 353bp | CCTGAGGATGCCACAGTGAGACACcatctgggtctggagggtccactgtgaggcagaggctgacctgta gagtccgacagtagacagaagttgggcaaaagcctgatttgaggaagttttgggcttcaagagtcagccacgaggc aggcactaggcctggaaatggcctcacagtcatgagttgggcctaaatgggccactgtgagggaggagctgtgcct gttgaggctgctggcaggcaggcagaaatttggcctggggcagctgccatgaggcaagagctgggcctggaaaaa gcccctgggaggcaagagcagggcctgcagaggCTGTTCTCAAGTCAAAGCTGGGCC |
| 35 | chr1:138356+138708 353bp | CCTGAGGATGCCACAGTGAGACACcatctgggtctggagggtccactgtgaggcagaggctgacctgta gagtccgacagtagacagaagttgggcaaaagcctgatttgaggaagttttgggcttcaagagtcagccacgaggc aggcactaggcctggaaatggcctcacagtcataagttgggcctaaatgggccactgtgagggaggagctgtgcct gttgaggctgctggcaggcaggcagaaatttggcctggggcagctgccatgaggcaagagctgggcctggaaaaa gccctgggaggcaagagcagggcctgcagaggCTGTTCTCAAGTCAAAGCTGGGCC |
| 36 | chr4:119408800+119409151 352bp | CCTGAGGATGCCACAGTGAGACACcatctgggtctgcagggtccactgtgaggcagaggctggcctgta gagtccgacagtagacacaagttgggcaaaaggctgatttgaggaagttttgggcttcaagagtcagccaggaggc aggcactaggcctggaaatggcccgacagtcatgagttgggcctaaatgggccaccgtgagggaggagctgtgcct gttgaggctgctggcaggcaggaagaaatttggcctgaggcagctgccatgaggcaagagctgggcttggaaaag cccctgggaggcaagagcaggcctgcagaggCTGTTCTCAAGTCAAAGCTGGGCC |
| 37 | chr7:56830262+56830613 352bp | CCTGAGGATGCCACAGTGAGACACcatctgggtctggagggtccactgtgaggcagaggctggcctgta gagtccaacagtagacagaagttgagcaaaaggctaatttcaggaagttttgggcttcaagagtcagccaggaggc aggcactaggcctggaaatggcccgacagtcatgagttgggcctaaatgggccactgtgagggaggagctgtgcct gttgaggctgctggcaggcaggcagaaacttggcctggggcagctgccatgagacaagagctgggcctggagaag ccctgagaggtaagagcagggcctgcagaggCTGTTCTCAAGTCAAAGCTGGGCC |
| 38 | chr7:56377197+56377548 352bp | CCTGAGGATGCCACAGTGAGACACcatctgggtctggagggtccactgtgaggcagaggctggcctgta gagtccgacagtagacagaagttgggcaaaaggctgatttgaggaagttttgggcttcaagagtcagccaggaggc aggcactaggcctggaaatggcccgacagtcatgagttgggcctaaatgggccactgtgagggaggagctgtgcct gttgaggctgctggcaggcaggcagaaacttggcctggggcagccgccatgaggcaagagctgggcctggagaag ccctgggaggcaagagcacggcctgcagaggCTGTTCTCAAGTCAAAGCTGGGCC |
| 39 | chr7:55746723+55747074 352bp | CCTGAGGATGCCACAGTGAGACACcatctgggtctggagggtccactgtgaggcagaggctggcctgta gagtccgacagtagacagaagttgggcaaaaggctgatttgaggaagttttgggcttcaagagtcagccaggaggc aggcactaggcctggaaatggcccgacagtcatgagttgggcctaaatgggccactgtgagggaggagctgtgcct gttgaggctgctggcaggcaggcagaaacttggcctggggcagccgccatgaggcaagagctgggcctggagaag ccctgggaggcaagagcacggcctgcagaggCTGTTCTCAAGTCAAAGCTGGGCC |

(table continues on next page)

Fig. 6: Sequences (continued from prior page)

| 40 | chrUn_KI270745v1:20310-20662 353bp | CCTGAGGATGCCACAGTGAGACACcatctgggtctggagggtccactgtgaggcagaggctgacctgtagagtccgacagtagacagaagttgggcaaaaggctgatttgaggaagttttgggcttcaagagtcagccacgaggcaggcactaggcctggaaatggcctcacagtcatgagttgggcctaaatgggccactgtgagggaggagctgtgcctgttgaggctgctggcaggcaggcagaaatttggcctggggcagctgccatgaggcaagagctgggcctggaaaaagccccctgggaggcaagagcagggcctgcagaggCTGTTCTCAAGTCAAAGCTGGGCC |
| --- | --- | --- |
| 41 | chr16:90167120-90167471 352bp | CCTGAGGATGCCACAGTGAGACACcatctgagtctggagggtccactgtgaggcagaggctggcctgtagagtccaacagtagacagaagttgggcaaaaggctgatttgaggaagttttgggcttcaagagtcagccacgaggcaggcactaggcctggaaatggcctcacagtcatgagttgggcctaaatgggccactgtgagggaggagctgtgcctgttgaggctgctggcaggcaggcagaaatttggcctgggcagctgccacgaggcaagagctgggcctggaaaaagccccctgggaggcaagagcagggcctgcagaggCTGTTCTCAAGTCAAAGCTGGGCC |
| 42 | chr1:227968529-227968881 353bp | CCTGAGGATGCCACAGTGAGACACcatctgggtctggagggtccactgtgaggcagaggctggcctgtagagtccgacagtagacagaagttgggcaaaaggctgatttgaggaagttttgggcttcaagagtcagccacgaggcaggcactaggcctggaaatggcccgacagtcatgagttgggcctaaatgggccactgtgagggaggagctgtgcctgttgaggctgctggcaggcaggcagaaatttggcctggggcagctgccatgaggcaggagctgggtctggaaaaagccccctgggaggcaagagcagggcctgcagaggCTGTTCTCAAGTCAAAGCTGGGCC |
| 43 | chr4:118631428-118631783 356bp | CCTGAGGATGCCACAGTGAGACACcatctgggtctggagggtccactgtgaggcagaggctggcctgtagagtccgacagtagacagaagttaggcaaaaggctgatttgaggaagttttgggcttcaagaaagtcagccaggaggcaggcactaggcctggaaatggcccgacagtcatgagtggggcctaaatgggccactgtgagggaggagctgtgcctgttgaggctgctggcaggcaggaagaaatttggcctggggcagctgccatgaggcaagagctgggcttgaaaagccccctgggaggcaagagcagggcctgcagaggCTGTTCTCAAGTCAAAGCTGGGCC |
| 44 | chr5:181325041-181325393 353bp | CCTGAGGATGCCACAGTGAGACACcatctgggtctggagggtccactgtgaggcagaggctgacctgtagagtccgacagtagacagaagttgggcaaaagcctgatttgaggaagttttgggcttcaagagtcagccacgaggcaggcactaggcctggaaatggcctcacagtcatgagttgggcctaaatgggccactgtgagggaggagctgtgcctgttgaggctgctggcaggcaggcagaaatttggcctggggcagctgccatgaggcaagagctgggcctggaaaaagccccctgggaggcaagagcagggcctgcagaggCTGTTCTCAAGTCAAAGCTGGGCC |
| 45 | chr7:128652162-128652514 353bp | aCTGAGGATGCCACAGTGAGACACcatctgggtctggagggtccactgtgaggcagaggctggcctgtagagtccgacagtagacagaagttgggcaaaaggctgatttgaggaagttttgggcttcaagagtcagccacgaggcaggcactaggcctggaaatggcccgacagtcatgagttgggcctaaatgggccactgtgagggaggagctatgcctgttgaggctgctggcaggcaggcagaaatttggcctggggcagctgccatgaggcaagagctgggcctggaaaaagccccctgggaggcaagagcagggcctgcagaggCTGTTCTCAAGTCAAAGCTGGGCC |
| 46 | chr7:63746403-63746754 352bp | CCTGAGGATGCCACAGTGAGACACcatctgggtctggagggtccactgtgaggcagaggctggcctgtagagtccgacagtagacagaagttgagcaaaaggctaatttcaggaagttttgggcttcaagagtcagccaggaggcaggcactaggcctggaaatggcccgacagtcatgagttgggcctaaatgggccactgtgagggaggagctgtgcctgttgaggctgctggcaggcaggcagaaacttggcctggagcagcttccatgagacaagagctgggcctggagaagcccctgagaggtaagaggagggcctgcagaggCTGTTCTCAAGTCAAAGCTGGGCC |

(table continues on next page)

Fig. 6: Sequences (contined from prior page)

| 47 | chr7:458 08475-4580882 6 352bp | CCTGAGGATGCCACAGTGAGACACcatctgggtctggagggtccactgtgaggcagaggctggcctgta gagtccgacagtagacagaagttgggcaaaaggctgatttgaggaagttttgggcttcaagagtcagccaggaggc aggcactaggcctggaaatggcccgacagtcatgagttgggcctaaatgggccactgtgagggaagagctgtgcct gttgaggctgctggcaggcaggcagaaacttggcctggggcagccgccatgaggcaagagctgggcctggagaag ccctgggaggcaagagcagggcctgcagaggCTGTTCTCAAGTCAAAGCTGGGCC |

METHOD FOR DETERMINING NUCLEIC ACID DEGRADATION IN A SAMPLE IN WHICH AT LEAST TWO OVERLAPPING AMPLICONS ARE PRODUCED AND TWO PROBES ARE USED IN THE METHOD

FIELD OF INVENTION

The present invention is in the field of molecular biology, diagnostics, and more particular, in the field of analytical and forensic sciences. Furthermore, the invention is in the field of nucleic acid amplification and quantification, more specifically in the field of DNA quantification and assessment of DNA degradation and integrity.

BACKGROUND

DNA based diagnostic methods are of rising importance in many areas, for example in the fields of diagnostic-, genetic-, forensic-, and food testing or for the detection of genetically modified organisms (GMO).

The determination of the quantity of DNA recovered from forensic samples as well as from other samples is a critical step in the overall DNA typing process, but also in the detection of DNA in various other fields of science. A narrow range of input DNA from 0.5 to 2 ng is often needed to produce optimal results with for example multiplex DNA typing kits. Therefore, in order to ensure that a positive result is a positive result and/or a negative result is a negative result due to the absence of DNA, quantification of DNA is of absolute importance. Furthermore, the quality of standards for forensic DNA testing laboratories requires human-specific DNA quantification. This is due to isolation techniques that can recover human DNA as well as bacterial and other exogenous DNA.

In addition, the quality of the DNA isolated from various sources can be compromised by degradation. This can influence the precision and validity of the assays applied on the tested DNA In forensics for example, human DNA integrity is of great importance and the quantification of the DNA is often put in front of a DNA fingerprinting analysis, e.g. in front of STR analyses or next-generation-sequencing (NGS). Currently, quantitative real-time PCR is a widely used method for DNA quantification since it offers various advantages. Such advantages are, within others, the species specific identification, a wide dynamic range as well as the ease of automation. For a typical short tandem repeats analysis markers range from about 100 bp up to about 450 bp, depending on the loci analyzed. Degraded DNA can lead to loss of amplification of the longest systems, or even to a complete failure of STR analysis.

As noted before, another important parameter in forensics and other disciplines is the degradation grade of the DNA that is analyzed. The extend of degradation is determined by the comparison of the amount of a short amplified DNA fragment with the amount of a long amplified DNA fragment obtaining a DNA degradation ratio (Goecker et al. 2016, Forensic Science International: "Comparison of Quantifiler®Trio and InnoQuant™ human DNA quantification kits for detection of DNA degradation in developed and aged fingerprints"). Furthermore, it is known from literature that the use of a short DNA fragment and one long DNA fragment exhibit a positive relationship between an increasing DNA degradation ratio and a loss in longer STR alleles. According to Goecker et al 2016, different quantification kits available utilize different targets for the DNA degradation assessment. When applied to the same degraded DNA sample, the use of different DNA targets in different qPCR systems may lead to significant different results for the sensitivity of DNA quantitation and the extent of DNA degradation.

A sensitive DNA quantification method to accurately detect and quantify DNA and in parallel to assess DNA degradation or integrity for a wide range of disciplines is therefore of great interest and there is a need for a method to encounter the drawbacks of the currently available kits.

The present invention solves the above identified problem and provides for the following solution as outlined below.

SUMMARY OF THE INVENTION

The present invention provides for a highly sensitive method for the assessment of the status of nucleic acid degradation and/or integrity of one or more nucleic acids in a sample, comprising the steps of amplifying at least two overlapping regions within at least one locus, and detecting the amount of the at least two amplification products through the use of at least two probes, wherein one probe binds to the region of overlap and the at least one other probe binds to a non-overlapping region.

The invention further relates to a method of designing primers and/or probes for amplifying at least two overlapping genomic regions within at least one nucleic acid template, wherein the locus that is amplified is a single copy locus (SCL) or multicopy locus (MLC).

The invention also relates to primer and primer pairs for amplifying said overlapping regions within at least one locus.

The primers and probes according to the invention may be in a kit. Hence, the invention also relates to a kit for assessing the status of nucleic acid degradation and/or integrity of one or more nucleic acids in a sample.

DETAILED DESCRIPTION OF THE INVENTION

As outlined above, the assessment of the integrity and/or degradation status of a nucleic acid template is of great importance and currently available methods do not sufficiently address and/or solve this problem. The present invention however, solves the problem and provides for a valuable system to assess the status of DNA degradation and/or integrity which is highly superior over existing methods and shows an astonishing sensitivity that has not been expected before.

In a first aspect of the present invention, the herein described method provides for the assessment of the status of nucleic acid degradation and/or integrity of one or more nucleic acids in a sample, comprising the steps of amplifying at least two overlapping regions from at least one nucleic acid template, and detecting the amount of the at least two amplification products through the use of at least two probes, wherein one probe binds to the region of overlap and the at least one other probe binds to a non-overlapping region.

One novel key feature of the present invention is that the at least two overlapping regions are amplified by using at least one common primer.

The inventors surprisingly found that particularly good results are achieved when, the size of the amplification products of the at least two overlapping regions are between 60 base pairs and 2000 base pairs long.

Ideally, the amplification product of one region is between 60 base pairs and 200 base pairs long, more ideally between 80 and 150, and most ideally between 85 and 100 base pairs long. In one ideal embodiment, one of the amplification products is 91 base pairs long.

It is also preferred that the amplification product of a second region is between 200 and 2000 base pairs (bp) long, more preferred between 210 and 1500 bp, between 220 and 1000 bp, between 230 and 800 bp, between 240 and 500 bp, or between 250 and 400 bp. Most preferably, the amplification product of a second region is 353 base pairs long.

Astonishingly it has turned out that, if the amplification product of a second overlapping region is longer than the amplification product of a first overlapping region better results may be achieved.

Therefore, in another preferred embodiment according to the invention, at least one of the amplification products of the at least two overlapping regions is at least 30% longer than the other one.

If a third overlapping region is amplified, it is preferred that the amplification product generated is at least 30% longer than the second amplification product.

It was very surprising for the inventors that with the system and arrangement according to the invention, the degraded DNA can be detected with such a particular high sensitivity. Particularly preferred arrangements of the system are depicted in FIGS. 1 and 2. FIG. 4 for example, shows that the larger PCR system according to the invention already detects degraded DNA, i.e. shows a shift of 0.5 Ct when applied on fragmented DNA of 1500 bp length. With the system according to the invention, Ct values increase consistently over the fragment length. For the fragments tested as shown in FIG. 4, Ct values reach their maximum at 150 bp, with more than 8 Ct values compared to undegraded DNA. These particularly good effects of the system were not expected and as such, the present invention is therefore highly superior over existing methods. Examples of arrangements of prior art are shown in FIG. 3. The advantages of the method over prior art are illustrated in FIGS. 4 and 5.

In one aspect of the present invention, the locus that amplified is a single copy locus (SCL) or a multicopy locus (MLC) within the nucleic acid assessed for integrity and/or degradation.

In case the locus is a multicopy locus, it may be found on various chromosomes and may be present many times in the genome. This can further improve the detection sensitivity of the present method and may provide a further valuable advantage of the present method.

In another aspect according to the present invention, it is particularly useful that in parallel to the assessment of the status of DNA degradation and/or integrity of one or more nucleic acids in a sample, the one or more nucleic acids are quantified and/or detected.

The degradation status/integrity of DNA can be assessed by using for example, at least two differently sized genomic regions in a qPCR in one vessel. The amplified targets have to have equal amplification efficiencies, causing co-amplification of the targets with the same efficiency. In case of degraded DNA the mean length of the DNA fragments in the sample will decrease leading to a loss of efficiency in amplification of the longer PCR systems. The shorter the fragments in the degraded DNA sample the higher the differences in amplification efficiencies between the shorter and larger PCR systems will become. Hereby, the integrity of DNA or degradation status of the DNA can be expressed by a ratio of the quantification of the systems used. The ratio is designated as degradation index.

Therefore, in one aspect of the present invention, the status of DNA integrity and/or degradation is expressed by the ratio of the quantification of the at least two overlapping regions within the at least one locus.

As shown in FIG. 5, the method according to the invention shows a very high sensitivity for the detection of degraded DNA of various sizes. It was very astonishing for the inventors to find out that the present method shows a much higher sensitivity than existing systems, in particular, when measuring degraded DNA of small sized fragments.

As such, the method according to the invention also relates to a method wherein the degradation index is at least 1.5 times higher for degraded fragments of 200 bp length and the at least 2.5 times higher for degraded fragments of 150 bp length when compared to the other PCR systems measuring the DNA degradation status as detailed in the Example and as shown in the Figures.

Ideally, the method according to the invention obtains a degradation index of at least 10 when measuring degraded DNA of 200 bp length and of at least 60 when measuring degraded DNA of 150 bp length.

The degradation index can sensibly vary according to the concentration of DNA fragment in a degraded DNA sample.

In a particular embodiment, the method according to the present invention obtains a degradation index of at least 10 when measuring 2.3 ng/µl degraded DNA of 200 bp length and of at least 60 when measuring 2.3 ng/µl degraded DNA of 150 bp length.

Further specifics of the good results obtained in a method according to the invention are detailed in the Figure legends and Examples.

In different embodiments that are all equally preferred, the sample is selected from the group of genomic samples, such as human DNA or microbial DNA (e.g. bacterial, archaeal or fungal), food samples (e.g. animal or plant derived), environmental samples (e.g. containing microorganisms). The method according to the invention can also be used for human/animal pathogen testing (bacterial, fungal, oomycetes) and phytopathology (bacterial, fungal, oomycetes).

According to another embodiment, the sample subjected to the present method originates from one of the following specimens comprising whole blood, blood fractions, oral fluids, body fluids, human bioptic tissue or other parts of the human body upon availability for isolation of a genome. As used herein the terms "oral fluids" and "body fluids" refers to fluids that are excreted or secreted from the buccal cavity and from the body, respectively, from which a genome can be isolated. As a non-limiting example, oral and body fluids may comprise saliva, sputum, swab, urine.

In case of a forensic sample, the sample may comprise a mixture of male and female DNA wherein the amount of female DNA exceeds the amount of male DNA by several orders of magnitude. Thus, according to another embodiment, the sample comprises one or more additional nucleic acids originating from a different genome. As used herein, the term "different genome" refers to genome isolated from a different subject, generally identified as female DNA.

According to another embodiment of the present invention, the amplification method is a polymerase chain reaction (PCR) or a quantitative real-time PCR reaction and the amount of nucleic acid determined is quantified either during the amplification process or as an end point measurement at the end of the amplification reaction.

The amplification reaction according to the present method may be either a non-isothermal method or an isothermal method.

The non-isothermal amplification method may be selected from the group of polymerase chain reaction (PCR) (Saiki et al. Science (1985) 230: 1350-1354), quantitative real-time PCR (rtPCR), ligase chain reaction (LCR) (Landegren et al. Science (1988) 241: 1077-1080). Polymerase chain reaction amplification is preferred.

Using real-time PCR techniques, fluorescence is detected and measured in the real-time PCR thermocycler, and its geometric increase corresponding to exponential increase of the product is used to determine the threshold cycle (Ct) in each reaction.

A standard curve (plot of Ct value/crossing point against log of amount of standard) is generated using different dilutions of the standard. The Ct value of the unknown samples is compared with the standard curve, allowing calculation of the initial amount of the target. It is important to select an appropriate standard for the type of nucleic acid to be quantified. To generate a standard curve, at least 5 different amounts of the standard should be quantified, and the amount of unknown target should fall within the range of the standard curve. Hence, in one embodiment also the above quantification steps are performed.

The isothermal amplification method may be selected from the group of helicase-dependent amplification (HDA) (Vincent et al. EMBO Rep (2004) 5(8): 795-800), thermostable HDA (tHDA) (An et al. J. Biol. Chem. (2005) 280(32): 28952-28958), strand displacement amplification (SDA) (Walker et al. Nucleic Acids Res. (1992) 20(7): 1691-1696), multiple displacement amplification (MDA) (Dean et al. Proc. Natl. Acad. Sci. USA (2002) 99(8): 5261-5266), rolling-circle amplification (RCA) (Liu et al. J. Am. Chem. Soc. (1996) 118: 1587-1594), restriction aided RCA (Wang et al. Genome Res (2004) 14: 2357-2366), single primer isothermal amplification (SPIA) (Dafforn et al. Biotechniques (2004), 37(5): 854-857), transcription mediated amplification (TMA) (Vuorinen et al. J. Clin. Microbiol. (1995) 33: 1856-1859), nicking enzyme amplification reaction (NEAR) (Maples et al. US2009017453), exponential amplification reaction (EXPAR) (Van Ness et al. Proc. Natl. Acad. Sci. USA (2003) 100(8): 4504-4509), loop mediated isothermal amplification (LAMP) (Notomi et al. Nucleic Acids Res. (2000) 28(12): e63), recombinase polymerase amplification (RPA) (Piepenburg et al. PloS Biol. (2006) 4(7): 1115-1120), nucleic acid sequence based amplification (NASBA) (Kievits et al. J. Virol. Methods (1991) 35: 273-286), smart-amplification process (SMAP) (Mitani et al. Nat. Methods (2007) 4(3): 257-262).

By "isothermal amplification reaction" in context of the present invention it is meant that the temperature does not significantly change during the reaction. In a preferred embodiment the temperature of the isothermal amplification reaction does not deviate by more than 10° C., preferably by not more than 5° C., even more preferably not more than 2° C. during the main enzymatic reaction step where amplification takes place.

Depending on the method of isothermal amplification of nucleic acids different enzymes are required for the amplification reaction. Known isothermal methods for amplification of nucleic acids are the above mentioned, wherein the at least one mesophilic enzyme for amplifying nucleic acids under isothermal conditions is selected from the group consisting of helicase, mesophilic polymerases, mesophilic polymerases having strand displacement activity, nicking enzymes, recombination proteins, ligases, glycosylases and/or nucleases.

"Helicases" are known by those skilled in the art. They are proteins that move directionally along a nucleic acid phosphodiester backbone, separating two annealed nucleic acid strands (e.g. DNA, RNA, or RNA-DNA hybrid) using energy derived from hydrolysis of NTPs or dNTPs. Based on the presence of defined helicase motifs, it is possible to attribute a helicase activity to a given protein. The skilled artisan is able to select suited enzymes with helicase activity for the use in a method according to the present invention. In a preferred embodiment the helicase is selected from the group comprising helicases from different families: superfamily I helicases (e.g. dda, perA, F-plasmid tral protein helicase, uvrD), superfamily II helicases (e.g. recQ, NS3-helicase), superfamily III helicases (e.g. AAV rep Helicase), helicases from DnaB-like superfamily (e.g. T7 phage helicase) or helicases from Rho-like superfamily.

The amplification methods will comprise buffers, dNTPs or NTPs in addition to the enzymes required.

As used herein, the term "dNTP" refers to deoxyribonucleoside triphosphates. Non-limiting examples of such dNTPs are dATP, dGTP, dCTP, dTTP, dUTP, which may also be present in the form of labelled derivatives, for instance comprising a fluorescent label, a radioactive label, a biotin label. dNTPs with modified nucleotide bases are also encompassed, wherein the nucleotide bases are for example hypoxanthine, xanthine, 7-methylguanine, inosine, xanthinosine, 7-methylguanosine, 5,6-dihydrouracil, 5-methylcytosine, pseudouridine, dihydrouridine, 5-methylcytidine. Furthermore, ddNTPs of the above-described molecules are encompassed in the present invention.

As used herein, the term "NTP" refers to ribonucleoside triphosphates. Non-limiting examples of such NTPs are ATP, GTP, CTP, TTP, UTP, which may also be present in the form of labelled derivatives, for instance comprising a fluorescent label, a radioactive label, a biotin label.

According to another embodiment of the present invention, the amplification reaction comprises, (a) Tris-HCl at a pH of between 8 and 8.8 (at 20° C.) and/or, (b) potassium salt selected from the group of, potassium chloride and potassium sulphate and/or, (c) an ammonium salt, preferably ammonium chloride or ammonium sulphate and/or, (d) magnesium chloride and/or, (e) a hot-start polymerase.

Preferably, the concentration of Tris-HCl is in the range from 10 to 100 mM, most preferably in the range from 20 to 70 mM, the concentration of r is in the range from 1-25 mM, most preferred in the range from 2.5 to 20 mM, the concentration of $NH_4^+$ in range from 1 to 40 mM, most preferred in the range from 2.5 to 30 mM, and a concentration of $Mg^{2+}$ of 0, 5 mM to 8 mM in excess to the concentration of the four dNTP's, most preferred a concentration of $Mg^{2+}$ of 0, 7 mM to 5 mM in excess to the concentration of the four dNTP's, a hot-start polymerase, preferentially a hot-start polymerase allowing a hot-start time of less than 5 min, most preferred below 2 min.

Overall, the method according to the invention shows an improved sensibility over prior art and other commercially available methods. In particular, the present method provides for a short run time, good accuracy, and low sensitivity to inhibitors.

Another aspect of the present invention relates to a method of designing primers and or probes for assessing of the status of nucleic acid degradation and/or integrity of one or more nucleic acids in a sample.

The primers can be used for amplifying at least two overlapping genomic regions within at least one genomic locus, wherein the locus that is amplified is a single copy locus (SCL) or multicopy locus (MLC).

In a preferred embodiment, the primers for amplifying at least two overlapping genomic regions, comprise primers that differ from SEQ ID NO. 1 to 3 by no more than 5 nucleotides over a stretch of 20 nucleotides.

It is further preferred that the primers comprise a sequence selected from the group of SEQ ID NO: 1 to 3.

The probes according to the invention can be used for the detection of the amount of at least two overlapping amplification products, wherein one probe binds to the region of overlap and the at least one other probe binds to a non-overlapping region.

Preferably, the probes comprise probes that differ from a sequence selected from the group of SEQ ID NO. 4 and 5 by no more than 5 nucleotides over a stretch of 20 nucleotides. In a further preferred embodiment, the probes comprise a sequence selected from the group of SEQ ID NO. 4 and 5.

In one aspect according to the invention, the primers and probes bind under stringent conditions to a sequence that shares at least 80% sequence identity to a sequence selected from the group of SEQ ID NO. 6 to 47 over a stretch of 80 base pairs, or to a reverse complement thereof.

Preferably the primers and probes bind to a sequence selected from the group of SEQ ID NO: 6 to 47, or to a reverse complement thereof.

Preferably, the primers bind to a sequence selected from the group of SEQ ID NO: 6 to 47.

A further embodiment of the present invention relates to the use of probes and/or primers in a method for assessment of the status of nucleic acid degradation and/or integrity of one or more nucleic acids in a sample according to the first aspect of the present invention.

According to another aspect of the present invention, a kit for assessing of the status of nucleic acid degradation and/or integrity is disclosed, the kit comprising the primers and probes as described above.

The present invention also relates to a kit comprising at least two primers and at least two probes that bind under stringent conditions to a sequence that shares at least 80% sequence identity to a sequence selected from the group of SEQ ID NO. 6 to 47 over a stretch of 80 base pairs, or a reverse complement thereof.

Preferably, the kit comprises at least two primers and at least two probes that bind to a sequence selected from the group of SEQ ID NO: 6 to 47, or a reverse complement thereof.

The invention also relates to a kit for assessing of the status of DNA degradation and/or integrity of one or more nucleic acids of a genome in a sample comprising at least two primers that differ from SEQ ID NO. 1 to 3 by no more than 5 nucleotides over a stretch of 20 nucleotides.

It is preferred that such a kit comprises at least two primers selected from the group of SEQ ID NO: 1 to 3.

Such a kit may comprise, in addition, at least two probes comprising the sequences of SEQ ID NO: 4 and 5.

In a further embodiment, the kit disclosed herein is used in a method for assessment of the status of nucleic acid degradation and/or integrity of one or more nucleic acids in a sample according to the first aspect of the present invention.

The kit can be used for amplifying at least two overlapping genomic regions within at least one genomic locus, wherein the locus that is amplified is a single copy locus (SCL) or multicopy locus (MLC).

In any case, a kit according to the invention is an optimized combination of target, probes and primer sequences.

EXAMPLES

The following example are used in conjunction with the Figures and Tables to illustrate the invention.

Description of Experiments for Ibtaining the Results Depicted in FIGS. 4 and 5

Environmental degradation may occur with forensic casework sample and is a typical challenge in routine genetic fingerprinting. Data presented here for the invention demonstrate the performance of the newly developed system for accurate DNA degradation detection.

Male genomic DNA was sheared with a Covaris™ 5220 Focused-ultrasonicator to an average fragment size of 1500 bp, 500 bp, 400 bp, 300 bp, 200 bp and 150 bp and 4.6 ng of each was tested with the invention for DNA degradation detection FIG. 4 (A).

Shown in FIG. 4 (B) is U.S. Pat. No. 9,040,243 B2/EP 10178914 applied on the same subset of degraded DNA fragments. Depicted in FIGS. 4 (C) and (D) are commercially available kits from Supplier A and Supplier P, tested with the same subset and amount of fragmented DNA like in Figure (A).

The commercially available quantification kits were set up and analyzed as described in the respective handbooks. A serial dilution of human DNAs (isolated from human blood from anonymous donors using the QIAamp Investigator Kit) and mixtures thereof at the concentrations described was used as a template for all of the kits tested.

FIGURE LEGEND

FIG. 1: Two Genomic Regions Targeted on One Genomic Locus

Depicted is a schematic drawing of the invention targeting different genomic regions on one genomic locus. The smaller PCR system consists of primer 1 and 2 and an appropriate probe for detection in qPCR and targets genomic region A. The larger PCR system consists of the same primer 1 and primer 3 extending the first genomic region A for the desired length and forming the second genomic region AB, which harbours the whole genomic region A.

FIG. 2: Three Genomic Regions Targeted on One Genomic Locus

Depicted is a schematic drawing of how the invention can be further extended targeting further genomic regions on one genomic locus. The smaller PCR system consists of primer 1 and 2 and an appropriate probe for detection in qPCR and targets genomic region A. The larger PCR system consists of the same primer 1 and a primer 3 extending the first genomic region A for the desired length and forming the second genomic region AB, which harbours the whole genomic region A. The larger PCR system consist of primer 1 and primer 4 extending genomic region A and genomic region AB and forming genomic region ABC and harbouring genomic region A and genomic region AB.

FIG. 3: Schematic Drawings of State of the Art Solutions to Address DNA Degradation or Integrity A) Two Non-Overlapping Genomic Regions Targeted on One Genomic Locus FIG. 3 (A) shows a schematic drawing of targeting two genomic regions on a genomic locus, here a multi copy locus (Invention U.S. Pat. No. 9,040,243 B2, EP10178914). The smaller PCR system consists of an appropriate primer1pro15e system for detection in qPCR and targets genomic region D. The larger PCR system consists of an appropriate primer/probe system for detection in qPCR and targets genomic region E which is a separate but adjacent genomic region to genomic region D. Genomic region E does not harbour or overlap with genomic region D.

B) Two Genomic Regions Targeted on Different Genomic Loci

FIG. 3 (B) depicts an approach where different genomic regions from different genomic loci are targeted. The smaller PCR system consists of an appropriate primer/probe system targets genomic region F on genomic locus X. The larger PCR system consists of an appropriate primer/probe system that targets genomic region G on genomic locus Y.

FIG. 4: Different Measurement Methods of Degraded DNA in Humans

A) Method According to the Invention

The invention shows no increase for the Ct values for the smallest PCR system (90 bp) for compromised DNA with an average fragment length from 1500 bp, 500 bp and 400 bp. Only for 300 bp, 200 bp and 150 bp there is an increase of up to 1.42 Ct values. Surprisingly the larger PCR system (352 bp) shows already a shift of 0.5 Ct when applied on fragmented DNA of 1500 bp length. Furthermore, the Ct values increase consistently on every further tested fragment length from 500 bp, 400 bp, 300 bp, 200 bp to 150 bp, and reach their maximum at 150 bp with more than 8 Ct values compared to undegraded DNA. This allows for a precise assessment of the degradation or integrity status of the DNA.

B) Method According to U.S. Pat. No. 9,040,243 B2/EP 10178914

This graph shows the invention from U.S. Pat. No. 9,040,243 82/EP 10178914 applied on the same subset of degraded DNA fragments. The smallest PCR system (146 bp) shows already an increase for a fragment length of 1500 bp when compared to undegraded DNA. This difference increases with every further fragment length tested (500 bp, 400 bp, 300 bp, 200 bp and 150 bp). The longer PCR system (363 bp) shows an increase in Ct values when applied on the 1500 bp fragment length. The CT value increases further when the 500 bp fragment length was tested. For the 400 bp and 300 bp fragment lengths tested only a slightly increase in Ct values was observed while a detection for 200 bp fragments and 150 bp fragments completely failed.

C) Method According to Supplier A

Shown is a testing with the commercially available "Quantifiler® Trio DNA Quantification Kit" from Applied Biosystems/Thermo Scientific. Reactions were setup up according to manufacturer's handbook. The Quantifiler TRIO kit uses a small PCR system of 80 bp length and a larger PCR system of 214 bp length. When the kit was applied to the different fragment lengths only a slightly increase in Ct values was observed for the longer PCR system when used with the 1500 bp, 500 bp, 400 bp and 300 bp fragment lengths. Only for 200 bp and 150 bp fragments a significant increase in Ct values was observable. This limits dramatically the ability of the assay to assess the degradation status or integrity of the DNA tested.

D) Method According to Supplier P

Shown is a testing with the commercially available "PowerQuant™ System" from Promega. Reactions were setup up according to manufacturer's handbook. The PowerQuant™ System kit uses a small PCR system of 84 bp length and a larger PCR system of 294 bp length. When the kit was applied to the different fragment lengths a significant difference in Ct value increase was observed for the 1500 bp and 500 bp fragments and for the 200 bp and 150 bp fragments. However, the PCR systems fail to detect a significant difference between 500 bp, 400 bp and 300 bp.

FIG. 5: Comparison of Degradation Indices Between Different PCR Systems

Shown are the degradation indices (i.e. the ratio of the amount of short fragments vs. the amount of long fragments (human S/human L)) of the different systems tested.

Noticeably, the method according to the invention (second column) obtains much higher indices, in particular for the small fragments (a value of almost 80) compared to the other systems. This indicates a much higher sensitivity for the detection of degraded DNA. Highlighted in grey, are the fragment sizes, for which the degradation status cannot be properly assessed anymore when using the other commercially available kits (light grey) or the RGQD system (dark grey).

FIG. 6: Sequences

Shown are sequences for primers, probes and amplicons according to the invention. For amplicon sequences, the primer binding sites are indicated with capital letters.

The invention claimed is:

1. A method for assessing the status of nucleic acid degradation and/or the integrity of one or more nucleic acids in a sample, comprising the steps of:
   a. amplifying at least two overlapping regions within at least one locus, and
   b. detecting the amount of the at least two amplification products through use of at least two probes, wherein one of said at least two probes binds to one of said at least two overlapping regions and the other of the at least two probes binds to a non-overlapping region,
   wherein the method obtains a degradation index of at least 10 when measuring degraded DNA of 200 base pair (bp) length and of at least 60 when measuring degraded DNA of 150 bp length, and
   wherein said at least two probes have sequences that differ by no more than 5 nucleotides over a stretch of 20 nucleotides from SEQ ID NO. 4 and SEQ ID NO. 5, respectively.

2. The method according to claim 1, wherein the at least two overlapping regions are amplified using at least one common primer.

3. The method according to claim 1, wherein the size of the amplification products of the at least two overlapping regions are between 60 base pairs and 2000 base pairs long.

4. The method according to claim 1, wherein a first one of the at least two amplification products of the at least two overlapping regions is at least 30% longer than a second one of the at least two amplification products.

5. The method according to claim 4, wherein a third overlapping region is amplified, and wherein a third amplification product is at least 30% longer than the second one of the at least two amplification products.

6. The method according to claim 1, wherein the locus that is amplified is a single copy locus (SCL) or a multicopy locus (MLC) within the nucleic acid assessed for integrity and/or degradation.

7. The method according to claim 1, wherein in parallel to the assessment of the status of DNA degradation and/or integrity of one or more nucleic acids in a sample, the one or more nucleic acids are quantified and/or detected.

8. The method according to claim 1, wherein the sample is selected from the group consisting of genomic samples, environmental samples and food samples.

9. The method according to claim 1, wherein the amplification method is either a non-isothermal method or an isothermal method.

10. The method according to claim 9, wherein the amplification method is selected from the group consisting of quantitative real-time PCR (rtPCR), ligase chain reaction (LCR), strand displacement amplification (SDA), multiple displacement amplification (MDA), rolling-circle amplification (RCA), loop mediated isothermal amplification (LAMP), transcription mediated amplification (TMA), helicase-dependent amplification (HDA), smartamplification process (SMAP), single primer isothermal amplification (SPIA), nicking enzyme amplification reaction (NEAR), exponential amplification reaction (EXPAR), recombinase polymerase amplification (RPA) and nucleic acid sequence based amplification (NASBA).

11. The method according to claim 2, wherein the at least one common primer has a sequence that differs from a sequence selected from the group consisting of SEQ ID NO. 1, SEQ ID NO. 2 and SEQ ID NO. 3 by no more than 5 nucleotides over a stretch of 20 nucleotides.

12. A method for assessing the status of nucleic acid degradation and/or the integrity of one or more nucleic acids in a sample, comprising the steps of:
   a. amplifying at least two overlapping regions within at least one locus, and
   b. detecting the amount of the at least two amplification products through use of at least two probes, wherein one of said at least two probes binds to one of said at least two overlapping regions and the other of the at least two probes binds to a non-overlapping region,
   wherein the method obtains a degradation index of at least 10 when measuring degraded DNA of 200 base pair (bp) length and of at least 60 when measuring degraded DNA of 150 bp length,
   wherein the at least two overlapping regions are amplified using at least one common primer, and
   wherein the at least one common primer has a sequence that differs from a sequence selected from the group consisting of SEQ ID NO. 1, SEQ ID NO. 2 and SEQ ID NO. 3 by no more than 5 nucleotides over a stretch of 20 nucleotides.

13. The method according to claim 12, wherein the size of the amplification products of the at least two overlapping regions are between 60 base pairs and 2000 base pairs long.

14. The method according to claim 12, wherein a first one of the at least two amplification products of the at least two overlapping regions is at least 30% longer than a second one of the at least two amplification products.

15. The method according to claim 14, wherein a third overlapping region is amplified, and wherein a third amplification product is at least 30% longer than the second one of the at least two amplification products.

16. The method according to claim 12, wherein the locus that is amplified is a single copy locus (SCL) or a multicopy locus (MLC) within the nucleic acid assessed for integrity and/or degradation.

17. The method according to claim 12, wherein in parallel to the assessment of the status of DNA degradation and/or integrity of one or more nucleic acids in a sample, the one or more nucleic acids are quantified and/or detected.

18. The method according to claim 12, wherein the sample is selected from the group consisting of genomic samples, environmental samples and food samples.

19. The method according to claim 12, wherein the amplification method is either a non-isothermal method or an isothermal method.

20. The method according to claim 19, wherein the amplification method is selected from the group consisting of quantitative real-time PCR (rtPCR), ligase chain reaction (LCR), strand displacement amplification (SDA), multiple displacement amplification (MDA), rolling-circle amplification (RCA), loop mediated isothermal amplification (LAMP), transcription mediated amplification (TMA), helicase-dependent amplification (HDA), smartamplification process (SMAP), single primer isothermal amplification (SPIA), nicking enzyme amplification reaction (NEAR), exponential amplification reaction (EXPAR), recombinase polymerase amplification (RPA) and nucleic acid sequence based amplification (NASBA).

21. The method according to claim 12, wherein said at least two probes have sequences that differ by no more than 5 nucleotides over a stretch of 20 nucleotides from SEQ ID NO. 4 and SEQ ID NO. 5, respectively.

* * * * *

SEQUENCE LISTING

<160> NUMBER OF SEQ ID NOS: 47

<210> SEQ ID NO 1
<211> LENGTH: 24
<212> TYPE: DNA
<213> ORGANISM: Artificial Sequence
<220> FEATURE:
<223> OTHER INFORMATION: primer

<400> SEQUENCE: 1
cctgaggatg ccacagtgag acac          24

<210> SEQ ID NO 2
<211> LENGTH: 28
<212> TYPE: DNA
<213> ORGANISM: Artificial Sequence
<220> FEATURE:
<223> OTHER INFORMATION: primer

<400> SEQUENCE: 2
acttctgtct actgtcggac tctacagg          28

```
<210> SEQ ID NO 3
<211> LENGTH: 24
<212> TYPE: DNA
<213> ORGANISM: Artificial Sequence
<220> FEATURE:
<223> OTHER INFORMATION: primer

<400> SEQUENCE: 3
ggcccagctt tgacttgaga acag                                              24

<210> SEQ ID NO 4
<211> LENGTH: 24
<212> TYPE: DNA
<213> ORGANISM: Artificial Sequence
<220> FEATURE:
<223> OTHER INFORMATION: probe

<400> SEQUENCE: 4
tctggagggt ccactgtgag gcag                                              24

<210> SEQ ID NO 5
<211> LENGTH: 24
<212> TYPE: DNA
<213> ORGANISM: Artificial Sequence
<220> FEATURE:
<223> OTHER INFORMATION: probe

<400> SEQUENCE: 5
tccaggccca gctcttgcct catg                                              24

<210> SEQ ID NO 6
<211> LENGTH: 91
<212> TYPE: DNA
<213> ORGANISM: Homo sapiens

<400> SEQUENCE: 6
cctgaggatg ccacagtgag acaccatctg ggtctggagg gtccactgtg aggcagaggc       60
tggcctgtag agtccgacag tagacagaag t                                      91

<210> SEQ ID NO 7
<211> LENGTH: 91
<212> TYPE: DNA
<213> ORGANISM: Homo sapiens

<400> SEQUENCE: 7
cctgaggatg ccacagtgag acaccatctg ggtctggagg gtccactgtg aggcagaggc       60
tgacctgtag agtccgacag tagacagaag t                                      91

<210> SEQ ID NO 8
<211> LENGTH: 91
<212> TYPE: DNA
<213> ORGANISM: Homo sapiens

<400> SEQUENCE: 8
cctgaggatg ccacagtgag acaccatctg ggtctggagg gtccactgtg aggcagaggc       60
tgacctgtag agtccgacag tagacagaag t                                      91

<210> SEQ ID NO 9
<211> LENGTH: 91
<212> TYPE: DNA
<213> ORGANISM: Homo sapiens

<400> SEQUENCE: 9
```

```
cctgaggatg ccacagtgag acaccatctg ggtctggagg gtccactgtg aggcagaggc    60
tgacctgtag agtccgacag tagacagaag t                                   91

<210> SEQ ID NO 10
<211> LENGTH: 91
<212> TYPE: DNA
<213> ORGANISM: Homo sapiens

<400> SEQUENCE: 10
cctgaggatg ccacagtgag acaccatctg ggtctggagg gtccactgtg aggcagaggc    60
tggcctgtag agtccgacag tagacagaag t                                   91

<210> SEQ ID NO 11
<211> LENGTH: 91
<212> TYPE: DNA
<213> ORGANISM: Homo sapiens

<400> SEQUENCE: 11
cctgaggatg ccacagtgag acaccatctg ggtctggagg gtccactgtg aggcagaggc    60
tggcctgtag agtccgacag tagacagaag t                                   91

<210> SEQ ID NO 12
<211> LENGTH: 91
<212> TYPE: DNA
<213> ORGANISM: Homo sapiens

<400> SEQUENCE: 12
cctgaggatg ccacagtgag acaccatctg ggtctggagg gtccactgtg aggcagaggc    60
tgacctgtag agtccgacag tagacagaag t                                   91

<210> SEQ ID NO 13
<211> LENGTH: 91
<212> TYPE: DNA
<213> ORGANISM: Homo sapiens

<400> SEQUENCE: 13
cctgaggatg ccacagtgag acaccatctg ggtctggagg gtccactgtg aggcagaggc    60
tgacctgtag agtccgacag tagacagaag t                                   91

<210> SEQ ID NO 14
<211> LENGTH: 91
<212> TYPE: DNA
<213> ORGANISM: Homo sapiens

<400> SEQUENCE: 14
cctgaggatg ccacagtgag acaccatctg ggtctggagg gtccactgtg aggcagaggc    60
tgacctgtag agtccgacag tagacagaag t                                   91

<210> SEQ ID NO 15
<211> LENGTH: 91
<212> TYPE: DNA
<213> ORGANISM: Homo sapiens

<400> SEQUENCE: 15
cctgaggatg ccacagtgag acaccatctg ggtctgcagg gtccactgtg aggcagaggc    60
tggcctgtag agtccgacag tagacacaag t                                   91

<210> SEQ ID NO 16
<211> LENGTH: 91
```

```
<212> TYPE: DNA
<213> ORGANISM: Homo sapiens

<400> SEQUENCE: 16
cctgaggatg ccacagtgag acaccatctg ggtctggagg gtccactgtg aggcagaggc    60
tggcctgtag agtccgacag tagacagaag t                                   91

<210> SEQ ID NO 17
<211> LENGTH: 91
<212> TYPE: DNA
<213> ORGANISM: Homo sapiens

<400> SEQUENCE: 17
cctgaggatg ccacagtgag acaccatctg ggtctggagg gtccactgtg aggcagaggc    60
tggcctgtag agtccgacag tagacagaag t                                   91

<210> SEQ ID NO 18
<211> LENGTH: 91
<212> TYPE: DNA
<213> ORGANISM: Homo sapiens

<400> SEQUENCE: 18
cctgaggatg ccacagtgag acaccatctg ggtctggagg gtccactgtg aggcagaggc    60
tggcctgtag agtccgacag tagacagaag t                                   91

<210> SEQ ID NO 19
<211> LENGTH: 91
<212> TYPE: DNA
<213> ORGANISM: Homo sapiens

<400> SEQUENCE: 19
cctgaggatg ccacagtgag acaccatctg ggtctggagg gtccactgtg aggcagaggc    60
tgacctgtag agtccgacag tagacagaag t                                   91

<210> SEQ ID NO 20
<211> LENGTH: 91
<212> TYPE: DNA
<213> ORGANISM: Homo sapiens

<400> SEQUENCE: 20
cctgaggatg ccacagtgag acaccatctg ggtctggagg gtccactgtg aggcagaggc    60
tggcctgtag agtccgacag tagacagaag t                                   91

<210> SEQ ID NO 21
<211> LENGTH: 91
<212> TYPE: DNA
<213> ORGANISM: Homo sapiens

<400> SEQUENCE: 21
cctgaggatg ccacagtgag acaccatctg ggtctggagg gtccactgtg aggcagaggc    60
tggcctgtag agtccgacag tagacagaag t                                   91

<210> SEQ ID NO 22
<211> LENGTH: 91
<212> TYPE: DNA
<213> ORGANISM: Homo sapiens

<400> SEQUENCE: 22
cctgaggatg ccacagtgag acaccatctg ggtctggagg gtccactgtg aggcagaggc    60
```

-continued tggcctgtag agtccgacag tagacagaag t                                       91

<210> SEQ ID NO 23
<211> LENGTH: 91
<212> TYPE: DNA
<213> ORGANISM: Homo sapiens

<400> SEQUENCE: 23
cctgaggatg ccacagtgag acaccatctg ggtctggagg gtccactgtg aggcagaggc       60
tgacctgtag agtccgacag tagacagaag t                                       91

<210> SEQ ID NO 24
<211> LENGTH: 91
<212> TYPE: DNA
<213> ORGANISM: Homo sapiens

<400> SEQUENCE: 24
actgaggatg ccacagtgag acaccatctg ggtctggagg gtccactgtg aggcagaggc       60
tggcctgtag agtccgacag tagacagaag t                                       91

<210> SEQ ID NO 25
<211> LENGTH: 91
<212> TYPE: DNA
<213> ORGANISM: Homo sapiens

<400> SEQUENCE: 25
cctgaggatg ccacagtgag acaccatctg ggtctggagg gtccactgtg aggcagaggc       60
tggcctgtag agtccgacag tagacagaag t                                       91

<210> SEQ ID NO 26
<211> LENGTH: 91
<212> TYPE: DNA
<213> ORGANISM: Homo sapiens

<400> SEQUENCE: 26
cctgaggatg ccacagtgag acaccatctg ggtctggagg gtccactgtg aggcagaggc       60
tggcctgtag agtccgacag tagacagaag t                                       91

<210> SEQ ID NO 27
<211> LENGTH: 353
<212> TYPE: DNA
<213> ORGANISM: Homo sapiens

<400> SEQUENCE: 27
cctgaggatg ccacagtgag acaccatctg ggtctggagg gtccactgtg aggcagaggc       60
tggcctgtag agtccgacag tagacagaag ttgggcaaaa ggctgatttg aggaagtttt      120
gggcttcaag agtcagccac gaggcaggca ctaggcctgg aaatggcctg acagtcatga      180
gttgggccta aatgggccac tgtgagggag gagctgtgcc tgttgaggct gctggcaggc      240
aggcagaaat tcggcctggg gcagctgcca tgaggcaaga gctgggcctg gaaaaagccc      300
ctgggaggca agagcagggc ctgcagaggc tgttctcaag tcaaagctgg gcc             353

<210> SEQ ID NO 28
<211> LENGTH: 353
<212> TYPE: DNA
<213> ORGANISM: Homo sapiens

<400> SEQUENCE: 28
cctgaggatg ccacagtgag acaccatctg ggtctggagg gtccactgtg aggcagaggc       60

```
tgacctgtag agtccgacag tagacagaag ttgggcaaaa ggctgatttg aggaagtttt    120
gggcttcaag agtcagccac gaggcaggca ctaggcctgg aaatggcctc acagtcatga    180
gttgggccta aatgggccac tgtgagggag gagctgtgcc tgttgaggct gctggcaggc    240
aggcagaaat ttggcctggg gcagccgcca tgaggcaaga gctgggcctg gaaaaagccc    300
ctgggaggca agagcagggc ctgcagaggc tgttctcaag tcaaagctgg gcc           353

<210> SEQ ID NO 29
<211> LENGTH: 353
<212> TYPE: DNA
<213> ORGANISM: Homo sapiens

<400> SEQUENCE: 29
cctgaggatg ccacagtgag acaccatctg ggtctggagg gtccactgtg aggcagaggc     60
tgacctgtag agtccgacag tagacagaag ttgggcaaaa gcctgatttg aggaagtttt    120
gggcttcaag agtcagccac gaggcaggca ctaggcctgg aaatggcctc acagtcatga    180
gttgggccta aatgggccac tgtgagggag gagctgtgcc tgttgaggct gctggcaggc    240
aggcagaaat ttggcctggg gcagctgcca tgaggcaaga gctgggcctg gaaaaagccc    300
ctgggaggca agagcagggc ctgcagaggc tgttctcaag tcaaagctgg gcc           353

<210> SEQ ID NO 30
<211> LENGTH: 353
<212> TYPE: DNA
<213> ORGANISM: Homo sapiens

<400> SEQUENCE: 30
cctgaggatg ccacagtgag acaccatctg ggtctggagg gtccactgtg aggcagaggc     60
tgacctgtag agtccgacag tagacagaag ttgggcaaaa ggctgatttg aggaagtttt    120
gggcttcaag agtcagccac gaggcaggca ctaggcctgg aaatggcctc acagtcatga    180
gttgggccta aatgggccac tgtgagggag gagctgtgcc tgttgaggct gctggcaggc    240
aggcagaaat ttggcctggg gcagccgcca tgaggcaaga gctgggcctg gaaaaagccc    300
ctgggaggca agagcagggc ctgcagaggc tgttctcaag tcaaagctgg gcc           353

<210> SEQ ID NO 31
<211> LENGTH: 353
<212> TYPE: DNA
<213> ORGANISM: Homo sapiens

<400> SEQUENCE: 31
cctgaggatg ccacagtgag acaccatctg ggtctggagg gtccactgtg aggcagaggc     60
tggcctgtag agtccgacag tagacagaag ttgggcaaaa ggctgatttg aggaagtttt    120
gggcttcaag agtcagccac gaggcaggca ctaggcctgg aaatggcctg acagtcatga    180
gttgggccta aatgggccac tgtgagggag gagctgtgcc tgttgaggct gctggcaggc    240
aggcagaaat tcggcctggg gcagctgcca tgaggcaaga gctgggcctg gaaaaagccc    300
ctgggaggca agagcagggc ctgcagaggc tgttctcaag tcaaagctgg gcc           353

<210> SEQ ID NO 32
<211> LENGTH: 353
<212> TYPE: DNA
<213> ORGANISM: Homo sapiens

<400> SEQUENCE: 32
```

| | |
|---|---|
| cctgaggatg ccacagtgag acaccatctg ggtctggagg gtccactgtg aggcagaggc | 60 |
| tggcctgtag agtccgacag tagacagaag ttgggcaaaa ggctgatttg aggaagtttt | 120 |
| gggcttcaag agtcagccac gaggcaggca ctaggcctgg aaatggcccg acagtcatga | 180 |
| gttgggacta aatgggccac tgtgagggag gagctgtgcc tgttgaggct gctggcaggc | 240 |
| aagcagaaat ttggcctcgg gcagctgcca tgaggcaaga gctgggcctg gaaaaagccc | 300 |
| ctgggaggca agagcagggc ctgcagaggc tgttctcaag tcaaagctgg gcc | 353 |

<210> SEQ ID NO 33
<211> LENGTH: 353
<212> TYPE: DNA
<213> ORGANISM: Homo sapiens

<400> SEQUENCE: 33

| | |
|---|---|
| cctgaggatg ccacagtgag acaccatctg ggtctggagg gtccactgtg aggcagaggc | 60 |
| tgacctgtag agtccgacag tagacagaag ttgggcaaaa gcctgatttg aggaagtttt | 120 |
| gggcttcaag agtcagccac gaggcaggca ctaggcctgg aaatggactc acagtcatga | 180 |
| gttgggccta aatgggccac tgtgagggag gagctgtgcc tgttgaggct gctggcaggc | 240 |
| aggcagaaat ttggcctggg gcagctgcca tgaggcaaga gctgggcctg gaaaaagccc | 300 |
| ctgggaggca agagcagggc ctgcagaggc tgttctcaag tcaaagctgg gcc | 353 |

<210> SEQ ID NO 34
<211> LENGTH: 353
<212> TYPE: DNA
<213> ORGANISM: Homo sapiens

<400> SEQUENCE: 34

| | |
|---|---|
| cctgaggatg ccacagtgag acaccatctg ggtctggagg gtccactgtg aggcagaggc | 60 |
| tgacctgtag agtccgacag tagacagaag ttgggcaaaa gcctgatttg aggaagtttt | 120 |
| gggcttcaag agtcagccac gaggcaggca ctaggcctgg aaatggcctc acagtcatga | 180 |
| gttgggccta aatgggccac tgtgagggag gagctgtgcc tgttgaggct gctggcaggc | 240 |
| aggcagaaat ttggcctggg gcagctgcca tgaggcaaga gctgggcctg gaaaaagccc | 300 |
| ctgggaggca agagcagggc ctgcagaggc tgttctcaag tcaaagctgg gcc | 353 |

<210> SEQ ID NO 35
<211> LENGTH: 353
<212> TYPE: DNA
<213> ORGANISM: Homo sapiens

<400> SEQUENCE: 35

| | |
|---|---|
| cctgaggatg ccacagtgag acaccatctg ggtctggagg gtccactgtg aggcagaggc | 60 |
| tgacctgtag agtccgacag tagacagaag ttgggcaaaa gcctgatttg aggaagtttt | 120 |
| gggcttcaag agtcagccac gaggcaggca ctaggcctgg aaatggcctc acagtcataa | 180 |
| gttgggccta aatgggccac tgtgagggag gagctgtgcc tgttgaggct gctggcaggc | 240 |
| aggcagaaat ttggcctggg gcagctgcca tgaggcaaga gctgggcctg gaaaaagccc | 300 |
| ctgggaggca agagcagggc ctgcagaggc tgttctcaag tcaaagctgg gcc | 353 |

<210> SEQ ID NO 36
<211> LENGTH: 352
<212> TYPE: DNA
<213> ORGANISM: Homo sapiens

<400> SEQUENCE: 36

```
cctgaggatg ccacagtgag acaccatctg ggtctgcagg gtccactgtg aggcagaggc    60
tggcctgtag agtccgacag tagacacaag ttgggcaaaa ggctgatttg aggaagtttt   120
gggcttcaag agtcagccag gaggcaggca ctaggcctgg aaatggcccg acagtcatga   180
gttgggccta aatgggccac cgtgaggag gagctgtgcc tgttgaggct gctggcaggc   240
aggaagaaat ttggcctgag gcagctgcca tgaggcaaga gctgggcttg aaaagcccc   300 tgggaggcaa gagcagggcc tgcagaggct gttctcaagt caaagctggg cc          352
```

<210> SEQ ID NO 37
<211> LENGTH: 352
<212> TYPE: DNA
<213> ORGANISM: Homo sapiens

<400> SEQUENCE: 37

```
cctgaggatg ccacagtgag acaccatctg ggtctggagg gtccactgtg aggcagaggc    60
tggcctgtag agtccaacag tagacagaag ttgagcaaaa ggctaatttc aggaagtttt   120
gggcttcaag agtcagccag gaggcaggca ctaggcctgg aaatggcccg acagtcatga   180
gttgggccta aatgggccac tgtgaggag gagctgtgcc tgttgaggct gctggcaggc   240
aggcagaaac ttggcctggg gcagctgcca tgagacaaga gctgggcctg gagaagcccc   300
tgagaggtaa gagcagggcc tgcagaggct gttctcaagt caaagctggg cc          352
```

<210> SEQ ID NO 38
<211> LENGTH: 352
<212> TYPE: DNA
<213> ORGANISM: Homo sapiens

<400> SEQUENCE: 38

```
cctgaggatg ccacagtgag acaccatctg ggtctggagg gtccactgtg aggcagaggc    60
tggcctgtag agtccgacag tagacagaag ttgggcaaaa ggctgatttg aggaagtttt   120
gggcttcaag agtcagccag gaggcaggca ctaggcctgg aaatggcccg acagtcatga   180
gttgggccta aatgggccac tgtgaggag gagctgtgcc tgttgaggct gctggcaggc   240
aggcagaaac ttggcctggg gcagccgcca tgaggcaaga gctgggcctg gagaagcccc   300
tgggaggcaa gagcacggcc tgcagaggct gttctcaagt caaagctggg cc          352
```

<210> SEQ ID NO 39
<211> LENGTH: 352
<212> TYPE: DNA
<213> ORGANISM: Homo sapiens

<400> SEQUENCE: 39

```
cctgaggatg ccacagtgag acaccatctg ggtctggagg gtccactgtg aggcagaggc    60
tggcctgtag agtccgacag tagacagaag ttgggcaaaa ggctgatttg aggaagtttt   120
gggcttcaag agtcagccag gaggcaggca ctaggcctgg aaatggcccg acagtcatga   180
gttgggccta aatgggccac tgtgagggag gagctgtgcc tgttgaggct gctggcaggc   240
aggcagaaac ttggcctggg gcagccgcca tgaggcaaga gctgggcctg gagaagcccc   300
tgggaggcaa gagcacggcc tgcagaggct gttctcaagt caaagctggg cc          352
```

<210> SEQ ID NO 40
<211> LENGTH: 353
<212> TYPE: DNA
<213> ORGANISM: Homo sapiens -continued

```
<400> SEQUENCE: 40
cctgaggatg ccacagtgag acaccatctg ggtctggagg gtccactgtg aggcagaggc      60
tgacctgtag agtccgacag tagacagaag ttgggcaaaa ggctgatttg aggaagtttt     120
gggcttcaag agtcagccac gaggcaggca ctaggcctgg aaatggcctc acagtcatga    180
gttgggccta atgggccac tgtgagggag gagctgtgcc tgttgaggct gctggcaggc     240
aggcagaaat ttggcctggg gcagctgcca tgaggcaaga gctgggcctg gaaaaagccc    300
ctgggaggca agagcagggc ctgcagaggc tgttctcaag tcaaagctgg gcc            353

<210> SEQ ID NO 41
<211> LENGTH: 352
<212> TYPE: DNA
<213> ORGANISM: Homo sapiens

<400> SEQUENCE: 41
cctgaggatg ccacagtgag acaccatctg agtctggagg gtccactgtg aggcagaggc     60
tggcctgtag agtccaacag tagacagaag ttgggcaaaa ggctgatttg aggaagtttt    120
gggcttcaag agtcagccac gaggcaggca ctaggcctgg aaatggcctc acagtcatga    180
gttgggccta atgggccac tgtgagggag gagctgtgcc tgttgaggct gctggcaggc     240
aggcagaaat ttggcctggg cagctgccac gaggcaagag ctgggcctgg aaaaagcccc    300
tgggaggcaa gagcagggcc tgcagaggct gttctcaagt caaagctggg cc             352

<210> SEQ ID NO 42
<211> LENGTH: 353
<212> TYPE: DNA
<213> ORGANISM: Homo sapiens

<400> SEQUENCE: 42
cctgaggatg ccacagtgag acaccatctg ggtctggagg gtccactgtg aggcagaggc      60
tggcctgtag agtccgacag tagacagaag ttgggcaaaa ggctgatttg aggaagtttt    120
gggcttcaag agtcagccac gaggcaggca ctaggcctgg aaatggcccg acagtcatga    180
gttgggccta atgggccac tgtgagggag gagctgtgcc tgttgaggct gctggcaggc     240
aggcagaaat ttggcctggg gcagctgcca tgaggcagga gctgggtctg gaaaaagccc    300
ctgggaggca agagcagggc ctgcagaggc tgttctcaag tcaaagctgg gcc            353

<210> SEQ ID NO 43
<211> LENGTH: 356
<212> TYPE: DNA
<213> ORGANISM: Homo sapiens

<400> SEQUENCE: 43
cctgaggatg ccacagtgag acaccatctg ggtctggagg gtccactgtg aggcagaggc      60
tggcctgtag agtccgacag tagacagaag ttaggcaaaa ggctgatttg aggaagtttt    120
gggcttcaag aaagagtcag ccaggaggca ggcactaggc ctggaaatgg cccgacagtc    180
atgagtgggg cctaaatggg ccactgtgag ggaggagctg tgcctgttga ggctgctggc    240
aggcaggaag aaatttggcc tggggcagct gccatgagcc aagagctggg cttgaaaaag    300
cccctgggag gcaagagcag ggcctgcaga ggctgttctc aagtcaaagc tgggcc         356

<210> SEQ ID NO 44
<211> LENGTH: 353
<212> TYPE: DNA
<213> ORGANISM: Homo sapiens
```

<400> SEQUENCE: 44

```
cctgaggatg ccacagtgag acaccatctg gtctggagg gtccactgtg aggcagaggc      60
tgacctgtag agtccgacag tagacagaag ttgggcaaaa gcctgatttg aggaagtttt    120
gggcttcaag agtcagccac gaggcaggca ctaggcctgg aaatggcctc acagtcatga    180
gttgggccta aatgggccac tgtgagggag gagctgtgcc tgttgaggct gctggcaggc    240
aggcagaaat ttggcctggg gcagctgcca tgaggcaaga gctgggcctg aaaaagccc     300
ctgggaggca agagcagggc ctgcagaggc tgttctcaag tcaaagctgg gcc           353
```

<210> SEQ ID NO 45
<211> LENGTH: 353
<212> TYPE: DNA
<213> ORGANISM: Homo sapiens

<400> SEQUENCE: 45

```
actgaggatg ccacagtgag acaccatctg gtctggagg gtccactgtg aggcagaggc      60
tggcctgtag agtccgacag tagacagaag ttgggcaaaa ggctgatttg aggaagtttt    120
gggcttcaag agtcagccac gaggcaggca ctaggcctgg aaatggcccg acagtcatga    180
gttgggccta aatgggccac tgtgagggag gagctatgcc tgttgaggct gctggcaggc    240
aggcagaaat ttggcctggg gcagctgcca tgaggcaaga gctgggcctg aaaaagccc     300
ctgggaggca agagcagggc ctgcagaggc tgttctcaag tcaaagctgg gcc           353
```

<210> SEQ ID NO 46
<211> LENGTH: 352
<212> TYPE: DNA
<213> ORGANISM: Homo sapiens

<400> SEQUENCE: 46

```
cctgaggatg ccacagtgag acaccatctg gtctggagg gtccactgtg aggcagaggc      60
tggcctgtag agtccgacag tagacagaag ttgagcaaaa ggctaatttc aggaagtttt    120
gggcttcaag agtcagccag gaggcaggca ctaggcctgg aaatggcccg acagtcatga    180
gttgggccta aatgggccac tgtgagggag gagctgtgcc tgttgaggct gctggcaggc    240
aggcagaaac ttggcctgga gcagcttcca tgagacaaga gctgggcctg agaagcccc     300
tgagaggtaa gaggagggcc tgcagaggct gttctcaagt caaagctggg cc            352
```

<210> SEQ ID NO 47
<211> LENGTH: 352
<212> TYPE: DNA
<213> ORGANISM: Homo sapiens

<400> SEQUENCE: 47

```
cctgaggatg ccacagtgag acaccatctg gtctggagg gtccactgtg aggcagaggc      60
tggcctgtag agtccgacag tagacagaag ttgggcaaaa ggctgatttg aggaagtttt    120
gggcttcaag agtcagccag gaggcaggca ctaggcctgg aaatggcccg acagtcatga    180
gttgggccta aatgggccac tgtgagggaa gagctgtgcc tgttgaggct gctggcaggc    240
aggcagaaac ttggcctggg gcagccgcca tgaggcaaga gctgggcctg agaagcccc     300
tgggaggcaa gagcagggcc tgcagaggct gttctcaagt caaagctggg cc            352
```